United States Patent [19]

Harris

[11] Patent Number: 4,618,452
[45] Date of Patent: Oct. 21, 1986

[54] SPOT TEST FOR 1,3,5-TRIAMINO-2,4,6-TRINITROBENZENE, TATB

[75] Inventor: Betty W. Harris, Los Alamos, N. Mex.

[73] Assignee: The United States of America as represented by the United States Department of Energy, Washington, D.C.

[21] Appl. No.: 676,149

[22] Filed: Nov. 29, 1984

[51] Int. Cl.$^4$ .................. G01N 31/00; G01N 33/00
[52] U.S. Cl. .................. 252/408.1; 436/111; 436/117
[58] Field of Search .................. 252/408.1; 436/111, 436/117

[56] References Cited

PUBLICATIONS

T. Urbanski, S. Kwiatkowska & W. Kutkiewicz, "On the Colour Reaction of Polynitrocompounds (Janovsky Reaction)," Bull. Acad. Pol. Sci. 7, 397–398 (1959).
D. M. Colman, "Rapid Identification of Some Expolsives by the Use of Spot Tests," Mound Laboratory Publication, No. MLM–2051 (1973).
David M. Colman, "Paper Chromatography of Substituted Trinitrobenzenes," Analyt. Chem. 35, 652–654 (1963).
Donald D. Glover and Eleanore G. Kayser, "Quantitative Spectrophotometric Analysis of Polynitroaromatic Compounds by Reaction with Ethylene Diamine," Analyt. Chem. 40, 2055–2058 (1968).
James P. Heotis and Jesse W. Cavett, "Color Reaction for Determination of Some Meta-Dinitro Aromatic Compounds," Analyt. Chem. 31, 1977–1978 (1959).

*Primary Examiner*—John F. Terapane
*Assistant Examiner*—S. Wolffe
*Attorney, Agent, or Firm*—Samuel M. Freund; Paul D. Gaetjens; Judson R. Hightower

[57] ABSTRACT

A simple, sensitive and specific spot test for 1,3,5-triamino-2,4,6-trinitrobenzene, TATB, is described. Upon the application of the composition of matter of the present invention to samples containing in excess of 0.1 mg of this explosive, a bright orange color results. Interfering species such as TNT and Tetryl can be removed by first treating the sample with a solvent which does not dissolve much of the TATB, but readily dissolves these explosives.

11 Claims, No Drawings

SPOT TEST FOR 1,3,5-TRIAMINO-2,4,6-TRINITROBENZENE, TATB

The United States has rights in this invention pursuant to Contract No. W-7405-ENG-36 between the U.S. Department of Energy and the University of California.

BACKGROUND OF THE INVENTION

The present invention relates generally to the identification of materials bearing explosives and more particularly to a spot test for the identification of materials containing 1,3,5-triamino-2,4,6-trinitrobenzene, TATB.

TATB, 1,3,5-triamino-2,4,6-trinitrobenzene, is an important explosive having use in both the military and private sectors. Consequently, methods for determining the presence of this explosive in various materials are under investigation. Prior attempts to develop a spot test for high explosives containing TATB have failed since it is insoluble in most common solvents, and the test reagents have either been unstable or nonspecific. For example, among the reagents investigated for this purpose are di-n-butylamine/N,N-dimethyl formamide which did not give a positive test for TATB although it gave a positive result for other polynitroaromatics, ethylene diamine/dimethyl sulfoxide which was found not to be very selective, and diethylamine/dimethyl sulfoxide which lacks stability. Also tried was concentrated potassium hydroxide which also lacks selectivity, giving a positive test with hexahydro-1,3,5-trinitro-1,3,5-triazine and 1,3,5,7-tetranitro-1,3,5,7-tetrazacyclooctane. Moreover, it caused sufficient yellow coloration in certain plastic bonded explosives to give a false result with regard to a material's TATB content.

Some of the test procedures which have been found to produce characteristic colors for certain explosives are detailed in the following four references:

1. "Color Reaction for Determination of Some Meta-Dinitro Aromatic Compounds," by James P. Heotis and Jesse W. Cavett, Anal. Chem. 31, 1977 (1959);
2. "Paper Chromatography of Substituted Trinitrobenzenes," by David M. Colman, Anal. Chem. 35, 653 (1963);
3. "Quantitative Spectrophotometric Analysis of Polynitroaromatic Compounds by Reaction with Ethylenediamine," by Donald D. Glover and Eleonore G. Kayser, Anal. Chem. 40, 2055 (1968): and
4. "Rapid Identification of Some Explosives by the Use of Spot Tests," by D. M. Colman, Mound Laboratory Publication No. MLM-2051, (1973).

None of these references teach a test for TATB or describe how one might accomplish this task.

In "On the Colour Reaction of Polynitrocompounds," by T. Urbanski, S. Kwiatkowski, and W. Kuthkiewicz, Bull. Acad. Pol. Sci. 7, 397 (1959), the authors describe color reactions for several explosives. In particular, they dissolve the explosive of interest in acetone and add a potassium hydroxide solution to the solution. This reference teaches away from the subject invention in that TATB does not dissolve in acetone and therefore cannot be identified using the method disclosed therein.

SUMMARY OF THE INVENTION

Accordingly, it is an object of my invention to provide a sensitive, simple and selective identification procedure for materials containing 1,3,5-triamino-2,4,6-trinitrobenzene.

Another object of the present invention is to provide a composition of matter suitable for use in spot testing of materials for TATB content.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the method of this invention may include the steps of rinsing the material under investigation thoroughly with a solvent in which TATB is substantially insoluble in order to remove significant concentrations of explosive materials which might interfere with the subject spot test such as trinitrotoluene, TNT and 2,4,6-trinitrophenylmethylnitramine, Tetryl, forming a homogeneous suspension or solution of between 5 and 20 weight percent of a strong base, between 5 and 20 weight percent of water and the remainder a solvent for TATB, contacting the rinsed material under investigation with this suspension resulting therefrom. It should be mentioned that the several solvents found to dissolve TATB are immiscible with water so that the test solution must be shaken to form a suspension in order for the appropriate mixing to occur.

In a further aspect of the present invention, in accordance with its objects and purposes, the composition of matter hereof includes a mixture of between 5 and 20 weight percent of a strong base, between 5 and 20 weight percent of water, and the remainder a solvent for TATB.

Among the benefits and advantages of the subject invention are the ability to perform sensitive, simple and specific tests of materials for TATB content and the identification of this explosive in its pure form.

DETAILED DESCRIPTION OF THE INVENTION

The present invention includes a composition of matter and a method for its use in the identification of materials containing the explosive 1,3,5-triamino-2,4,6-trinitrobenzene, TATB. Collected dust samples or small samples from bulk materials are simply treated with the composition of matter according to the teachings of my invention. A bright orange color indicates the presence of TATB. Interfering explosives such as TNT and Tetryl can be removed from the sample under investigation by first treating the sample with a solvent for these materials such as acetone in which TATB is substantially insoluble. The remaining material will then give the characteristic color if TATB is present. Occasionally, explosives containing TATB are transported in the form of wax or plastic coated beads of the explosive material. Acetone or another suitable solvent can be used to dissolve the coating, thereby permitting the test chemicals to reach the TATB. As an alternative, the pellets of the explosive materials might be ground to a powder before the test for TATB is performed according to the method of the subject invention.

Having generally described the invention, the following specific examples are given as a further illustration thereof.

EXAMPLE I

A mixture of 5 g of KOH, 5 g of water and 90 g of dimethyl sulfoxide when shaken vigorously and contacted with materials containing TATB was found to give the characteristic bright orange color for TATB quantities in excess of 0.1 mg. The test liquid was found to give no reaction for kel-F, 1,3,5,7-tetranitro-1,3,5,7-tetrazacyclooctane, PETN, pentaerythritol tetranitrate, and RDX, hexahydro-1,3,5-trinitro-1,3,5-triazine. Tetryl and TNT were found to give red and purple colors, respectively. A strong solution of KOH was found to be nonspecific; i.e., it gave reactions with the nonreacting compounds mentioned hereinabove. However, the dimethyl sulfoxide dissolves sufficient TATB and base when the composition of the present invention is vigorously shaken to enable the color reaction to yield a readily identifiable color for TATB but not these other compounds. As described hereinabove, if TNT or Tetryl are suspected in the sample under investigation, the sample can be first treated with acetone or another solvent which readily dissolves these interfering species, but does not dissolve the TATB.

EXAMPLE II

A liquid mixture of 20 g of KOH, 5 g of water and 75 g of either dimethyl formamide or hexamethyl phosphortriamide was found to give the characteristic bright orange color when TATB in greater than 0.1 mg quantities was present; and no reaction for the compounds listed hereinabove, which did not react with the composition of matter of the subject invention containing dimethyl sulfoxide. Reaction with TNT and Tetryl producing colors characteristic of these explosives still occurred. As for the test described in Example I hereinabove, these interfering species can be removed using acetone or another suitable solvent. It is believed by the inventor that a more concentrated base must be used when using dimethyl formamide or hexamethyl phosphoramide since TATB is much less soluble in these solvents than in dimethyl sulfoxide.

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for the identification of materials containing 1,3,5-triamino-2,4,6-trinitrobenzene, said method comprising the steps of:
   a. rinsing the material thoroughly with a solvent in order to remove significant concentrations of explosive substances present in the materials under investigation in which the 1,3,5-triamino-2,4,6-trinitrobenzene is substantially insoluble;
   b. forming a homogeneous suspension of a liquid which comprises between 5 and 20 weight percent of a water-soluble strong base, between 5 and 20 weight percent of water and the remainder a solvent for 1,3,5-triamino-2,4,6-trinitrobenzene, the solvent for 1,3,5-triamino-2,4,6-trinitrobenzene having a slight solubility for the water with the water-soluble strong base dissolved therein;
   c. contacting said thoroughly rinsed material with said homogeneous suspension; and
   d. observing the color of the liquid resulting therefrom, whereby a bright orange color results if 1,3,5-triamino-2,4,6-trinitrobenzene is present in the material.

2. The method as described in claim 1, wherein said water-soluble strong base is selected from the group consisting of sodium hydroxide, potassium hydroxide, and barium hydroxide.

3. The method as described in claim 2, wherein said solvent for 1,3,5-triamino-2,4,6-trinitrobenzene includes dimethyl sulfoxide.

4. The method as described in claim 3, wherein said liquid suspension comprises about 5 weight percent of potassium hydroxide, approximately 5 weight percent of water, and the remainder dimethyl sulfoxide.

5. The method as described in claim 4, wherein said solvent in which the 1,3,5-triamino-2,4,6-trinitrobenzene is substantially insoluble includes acetone, whereby any explosives present in the material under investigation can be separated from the 1,3,5-triamino-2,4,6-trinitrobenzene.

6. The method as described in claim 2, wherein said liquid suspension comprises about 20 weight percent of potassium hydroxide, approximately 5 weight percent of water, and the remainder said solvent for 1,3,5-triamino-2,4,6-trinitrobenzene, wherein said solvent for 1,3,5-triamino-2,4,6-trinitrobenzene is selected from the group consisting of dimethyl sulfoxide, dimethyl formamide, and hexamethyl phosphoramide.

7. A method for the identification of materials containing 1,3,5-triamino-2,4,6-trinitrobenzene, but not 2,4,6-trinitrotoluene or 2,4,6-trinitrophenylmethylnitramine, said method comprising the steps of:
   a. forming a homogeneous suspension of a liquid which comprises between 5 and 20 weight percent of a water-soluble strong base, between 5 and 20 weight percent of water, and the remainder a solvent for 1,3,5-triamino-2,4,6-trinitrobenzene having a slight solubility for said water with said water-soluble strong base dissolved therein;
   b. contacting the material under investigation with said homogeneous suspension; and
   c. observing the color of the liquid resulting therefrom, whereby a bright orange color results if 1,3,5-triamino-2,4,5-trinitrobenzene is present in the material.

8. The method as described in claim 7, wherein said water-soluble strong base is selected from the group consisting of sodium hydroxide, potassium hydroxide, and barium hydroxide.

9. The method as described in claim 8, wherein said solvent for 1,3,5-triamino-2,4,6-trinitrobenzene includes dimethyl sulfoxide.

10. The method as described in claim 9, wherein said liquid suspension comprises about 5 weight percent of potassium hydroxide, approximately 5 weight percent of water, and the remainder dimethyl sulfoxide.

11. The method as described in claim 8, wherein said liquid suspension comprises about 20 weight percent of said water-soluble strong base, approximately 5 weight percent of water, and the remainder said solvent for 1,3,5-triamino-2,4,6-trinitrobenzene, wherein said solvent for 1,3,5-triamino-2,4,6-trinitrobenzene is selected from the group consisting of dimethyl sulfoxide, dimethyl formamide, and hexamethyl phosphoramide.

* * * * *